United States Patent [19]

Leonard

[11] Patent Number: 4,736,843

[45] Date of Patent: Apr. 12, 1988

[54] PACKING CASE FOR DENTAL CANAL INSTRUMENTS

[75] Inventor: Henri Leonard, Besancon, France

[73] Assignee: MICRO-MEGA S.A., Besancon, France

[21] Appl. No.: 20,516

[22] Filed: Mar. 2, 1987

[30] Foreign Application Priority Data

Jun. 12, 1986 [FR] France .................. 86 08508

[51] Int. Cl.$^4$ ................ B65D 81/18; B65D 85/20
[52] U.S. Cl. .................................. 206/369; 206/372; 206/459; 229/125.35
[58] Field of Search .............. 206/352, 361, 362, 363, 206/368–370, 379, 380, 459, 461, 526; 220/359; 229/125.35

[56] References Cited

U.S. PATENT DOCUMENTS

| | | | |
|---|---|---|---|
| 3,759,375 | 9/1973 | Nappi | 206/361 |
| 3,809,221 | 5/1974 | Compere | 206/461 |
| 4,015,709 | 4/1977 | Millet | 206/366 |
| 4,324,331 | 4/1982 | Ignasiak | 206/370 |
| 4,346,833 | 8/1982 | Bernhardt | 220/359 |

OTHER PUBLICATIONS

"Woodies Gift Fragrances", Advertising Supplement, *Washington Post*, Nov. 21, 1976.

*Primary Examiner*—Jimmy G. Foster
*Attorney, Agent, or Firm*—Robert E. Burns; Emmanuel J. Lobato

[57] ABSTRACT

This packing case comprises a support provided with a plurality of separate parallel cavities adapted to receive the dental canal instruments and a protection cover consisting of a self-adhesive sheet. This sheet of thin transparent and flexible material has a gripping edge parallel to the longitudinal axis of the cavities and this edge projects laterally from the support surface. By raising the sheet by means of the gripping edge the user can uncover the cavities one by one and thus pick up a selected instrument by simply turning the case upside down, the other instrument being retained in the case. With this packing case it is possible to pack various types of dental instruments such as files, reamers, drills, Hedstroem files, nerve broaches, etc., and the cover may also be used as a label carrying inscriptions concerning the type of dental instrument contained in the case.

1 Claim, 1 Drawing Sheet

PACKING CASE FOR DENTAL CANAL INSTRUMENTS

BACKGROUND OF THE INVENTION

1. Field of the Invention

The present invention relates to a packing case for dental canal instruments, which comprises a support in which separate parallel cavities are formed for receiving the dental instruments, and a protection cover.

2. The Prior Art

Various forms of embodiment of packing cases of this character are already known in the art, and in most instances these packing cases are provided with a rigid sliding or pivoting cover. However, these various forms of embodiment of prior art devices are difficult to handle, notably because the dental surgeon must be very careful, when the cover is raised or removed, so that he can pick up with one finger one of the small instruments contained in the support without dropping the other instruments, this operation being rather awkward for the practitioner who in many cases is in a hurry.

SUMMARY OF THE INVENTION

It is the essential object of the present invention to provide an improved packing case meeting all the desire safety and easy-handling requirements.

For this purpose, the packing case for dental canal instruments according to the present invention is characterised by the fact that the support cover consists of a relatively thin, self-adhesive sheet, preferably in the form of a transparent label carrying inscriptions concerning the type of dental canal instruments contained in the cavities or cells of the support, this sheet being provided with a gripping edge parallel to the longitudinal axis of the cavities and projecting somewhat from the support surface so that the sheet can easily be lifted off the support over an area corresponding to the selected cavity.

THE DRAWING

FIG. 1 is a perspective view of the packing case with the cover-forming sheet adhering thereto, and FIG. 2 is a view similar to FIG. 1 but showing the transparent sheet partly lifted off the support to provide access to the first cavity.

DESCRIPTION OF THE PREFERRED EMBODIMENT

Figure 1:
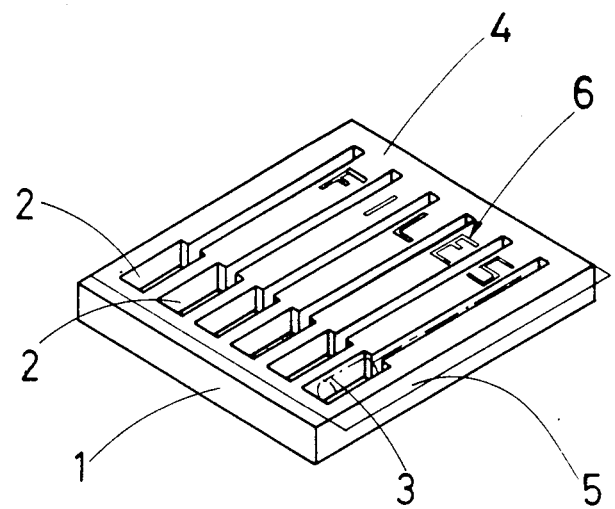
Figure 2:
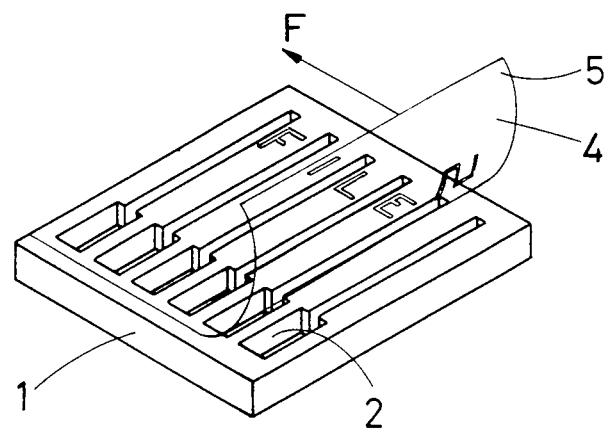

The packing case according to this invention comprises a rectangular support 1 having six (or any other suitable number) elongate cavities or cells 2 of similar configuration, disposed in parallel relationship. In fact, these cavities 2 correspond substantially to the contour of the dental instruments to be kept therein, namely a wider section corresponding to the handle and a relatively long and narrow section corresponding to the operative portion of the instrument. In FIG. 1, an instrument 3 is shown in dash and dot lines in its cavity 2.

The cover 4 consists of a transparent, self-adhesive sheet which, when all the instruments are disposed in the corresponding cavities 2, covers completely and protects the instruments. This sheet 4 comprises a lateral extension 5 projecting somewhat from one side of the support 1 and parallel to the axis of said cavities 2.

According to a preferred form of embodiment of the invention, this transparent sheet 4 constitutes at the same time a label on which inscriptions 6 concerning the various types of instruments contained in cavities 2 are printed or otherwise reproduced. In the case illustrated, the instruments 3 are files.

When the dental surgeon needs a particular instrument, he separates slightly the cover 4 from the support 1 by pulling the projecting edge 5, so as to gradually uncover the first cavity 2. Thus, the instrument nested in this cavity can be removed therefrom by simply turning the case 1 upside down, without any risk of dropping the other instruments, since they are still retained by the self-adhesive cover 4. When the dental surgeon needs another instrument from the same case, he simply uncovers the area corresponding to the second cavity, and so forth.

Packing cases of this type can be used with various types of dental canal instruments, notably files, reamers, drills, Hedstroem files, nerve broaches, etc., and their specifications may be printed on the label-forming cover 4.

I claim:

1. A packing case for dental canal instruments which comprises a rectangular support having an upper support surface and a plurality of upwardly-opening elongate instrument-receiving cavities disposed parallel to a side of said support and a protective cover consisting of a thin, transparent self-adhesive sheet overlying and releasably bonded to said support surface of said support and bearing indicia identifying instruments in said cavities, said sheet having a gripping edge portion extending beyond a side of said support parallel to said cavities for peeling said sheet from said surface progressively from said last-mentioned side of said support to uncover said cavities individually and successively for removal of individual instruments by gravity upon inversion of said support.

* * * * *